US008361051B2

(12) United States Patent
Ezeude

(10) Patent No.: US 8,361,051 B2
(45) Date of Patent: Jan. 29, 2013

(54) CALIBRATED MEDICINE MIXING ASSEMBLY AND ASSOCIATED METHOD

(76) Inventor: Enuma E. Ezeude, Brooklyn, NY (US)

( * ) Notice: Subject to any disclaimer, the term of this patent is extended or adjusted under 35 U.S.C. 154(b) by 719 days.

(21) Appl. No.: 12/383,628

(22) Filed: Mar. 27, 2009

(65) Prior Publication Data

US 2010/0174264 A1 Jul. 8, 2010

Related U.S. Application Data

(60) Provisional application No. 61/070,791, filed on Mar. 27, 2008.

(51) Int. Cl.
*A61B 19/00* (2006.01)
*A61M 5/32* (2006.01)

(52) U.S. Cl. .......................... 604/416; 604/403; 604/404

(58) Field of Classification Search .................... 604/82, 604/89, 403–416; 206/219–221, 568; 220/23.86–23.89, 503, 521; 215/DIG. 8
See application file for complete search history.

(56) References Cited

U.S. PATENT DOCUMENTS 4,282,863 A * 8/1981 Beigler et al. ................ 604/262
5,385,545 A * 1/1995 Kriesel et al. ................... 604/82

* cited by examiner

*Primary Examiner* — Philip R Wiest

(57) ABSTRACT

The calibrated medicine mixing assembly preferably includes a primary reservoir having a primary cavity adapted to receive the fluid. The primary reservoir preferably including calibrated fluid level indicia displayed on an outer surface. Such an assembly may further include a secondary reservoir preferably having a secondary cavity adapted to receive the powder agent. The secondary reservoir preferably including calibrated level indicia displayed on its outer surface. The secondary reservoir is further removably positioned into the primary reservoir such that a major surface area of the secondary reservoir is completely submerged inside the primary reservoir. A plurality of orifices may preferably be formed along a top region of the secondary reservoir, the orifices further situated inside the primary reservoir, thereby causing the secondary cavity to be in fluid communication with the primary cavity when the secondary reservoir is situated within the primary reservoir.

16 Claims, 4 Drawing Sheets

CALIBRATED MEDICINE MIXING ASSEMBLY AND ASSOCIATED METHOD

CROSS REFERENCE TO RELATED APPLICATIONS

This application claims the benefit of U.S. Provisional Application No. 61/070,791, filed Mar. 27, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to calibrated mixing containers and, more particularly, to a calibrated medicine mixing assembly for accurately mixing powder medication with fluid during administration of medicine.

2. Prior Art

Consumers who are health-conscious or who have certain medical needs desire to know the specific amount of certain chemical compounds that they are ingesting when consuming certain substances. For example, persons with diabetes, high blood pressure, or heart disease may desire to be sure that they do not consume more than an exact serving size amount of foodstuff, or a suitable dose of their medication. Various apparatuses have been proposed in the art for measuring a volume of a solid or liquid substance dispensed from a container.

For example, measuring spoons or cups are used for measuring a quantity of a substance being removed from a container. Although assumed to be effective for their intended purposes, the existing examples do not provide a convenient means of indicating on the container itself a volume of a liquid that has been consumed or that will be consumed momentarily.

Further, the existing prior art applications do not provide a structure by which a user may visually correlate consumption of amounts of pre-selected chemical compounds of the substance with consumption of a predetermined volume of the overall substance. For those required to take prescription medication that is in powdered form and must be mixed with a specific amount of fluid for consumption, the need for an accurate measuring means is even more crucial.

Accordingly, a need remains for calibrated medicine mixing assembly to overcome the above-noted shortcomings. The present invention satisfies such a need by providing an apparatus that is convenient and easy to use, is durable yet lightweight in design, is versatile in its applications, and ensures that virtually anyone can precisely measure-out the indicated volume of diluting agent for mixing medicine.

BRIEF SUMMARY OF THE INVENTION

In view of the foregoing background, it is therefore an object of the present invention to provide an apparatus for a calibrated medicine mixing assembly for assisting a user to accurately mix a powder agent with a fluid. These and other objects, features, and advantages of the invention are provided by a calibrated medicine mixing assembly and associated method.

The calibrated medicine mixing assembly preferably may include a primary reservoir having a primary cavity adapted to receive the fluid. The primary reservoir preferably including calibrated fluid level indicia displayed on an outer surface. Such an assembly may further include a secondary reservoir preferably having a secondary cavity adapted to receive the powder agent. The secondary reservoir preferably including calibrated level indicia displayed on its outer surface.

The secondary reservoir is further removably positioned into the primary reservoir such that a major surface area of the secondary reservoir is completely submerged inside the primary reservoir. A plurality of orifices may preferably be formed along a top region of the secondary reservoir, the orifices further situated inside the primary reservoir, thereby causing the secondary cavity to be in fluid communication with the primary cavity when the secondary reservoir is situated within the primary reservoir.

In one embodiment, the secondary reservoir may preferably be prohibited from laterally oscillating while seated within the primary reservoir such as for example when the assembly is held by a user. Each of the primary and secondary reservoirs may further include a top spout in fluid communication with a corresponding one of the primary and secondary cavities respectively.

A cap may further be removably coupled directly to a corresponding one of the top spouts. Further, the primary cavity may preferably extend downwardly from a top surface of the primary reservoir and suitably sized and shaped to receive the secondary reservoir therein.

Further, the secondary reservoir may include a unitary and continuous gasket positioned along an entire perimeter, the gasket flaring outwardly and away from the outer perimeter such that the gasket directly sits on the top surface when the secondary reservoir is situated within the primary reservoir. In this manner, the gasket may preferably act as a seal to prevent the risk of spillage when the assembly is inverted with the assembly held in place securely such as preferably with the index finger pressed against the top of the secondary spout and the thumb and other fingers holding the primary reservoir securely.

In another embodiment, the orifices are further disposed subjacent to the top surface of the primary reservoir to enable the powder agent and the fluid to mix when the primary and secondary reservoirs are repeatedly inverted. The top spout of the secondary reservoir further remains situated exterior of the primary reservoir while the secondary reservoir is situated within the primary cavity. In this way, the orifices remain spaced below the top spout and the top surface of the primary reservoir while the secondary reservoir is situated within the primary reservoir.

In a further embodiment, the secondary reservoir is removed from the primary reservoir when the secondary reservoir is axially displaced along a linear path registered parallel to a longitudinal length of the primary reservoir. The assembly further including a bottom-most surface of the secondary reservoir to remain spaced above a bottom-most surface of the primary cavity while the secondary reservoir is fully inserted into the primary reservoir such that the fluid contained within the primary cavity is able to freely travel beneath the secondary reservoir.

The invention further includes a method for accurately mixing a powder agent with a fluid, the method comprising the chronological steps of providing a primary reservoir preferably having a primary cavity, including calibrated fluid level indicia displayed on an outer surface. The invention may further include the second step of providing a secondary reservoir preferably having a secondary cavity and preferably including calibrated powder agent level indicia displayed on an outer surface and provided with a plurality of orifices formed along a top region.

In this way, the assembly may enable pouring the fluid and powder agent into the primary cavity and secondary cavity respectively and removably positioning the secondary reservoir into the primary reservoir such that a major surface area of the secondary reservoir is completely submerged inside the primary reservoir. This may preferably cause the secondary cavity to be in fluid communication with the primary cavity by situating the orifices inside the primary reservoir while the secondary reservoir is situated within the primary reservoir.

Such a method may preferably allow mixing the powder agent and the fluid by repeatedly inverting the primary and secondary reservoirs; and prohibiting the secondary reservoir from laterally oscillating while seated within the primary reservoir. Such a calibrated medicine mixing assembly is vital and advantageous in allowing a user to provide the unexpected and unpredictable benefit of accurately measuring a medicinal powder and a fluid in exact quantities and enabling the combination to be properly mixed without spillage when the assembly is repeatedly inverted so as to mix the ingredients thoroughly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
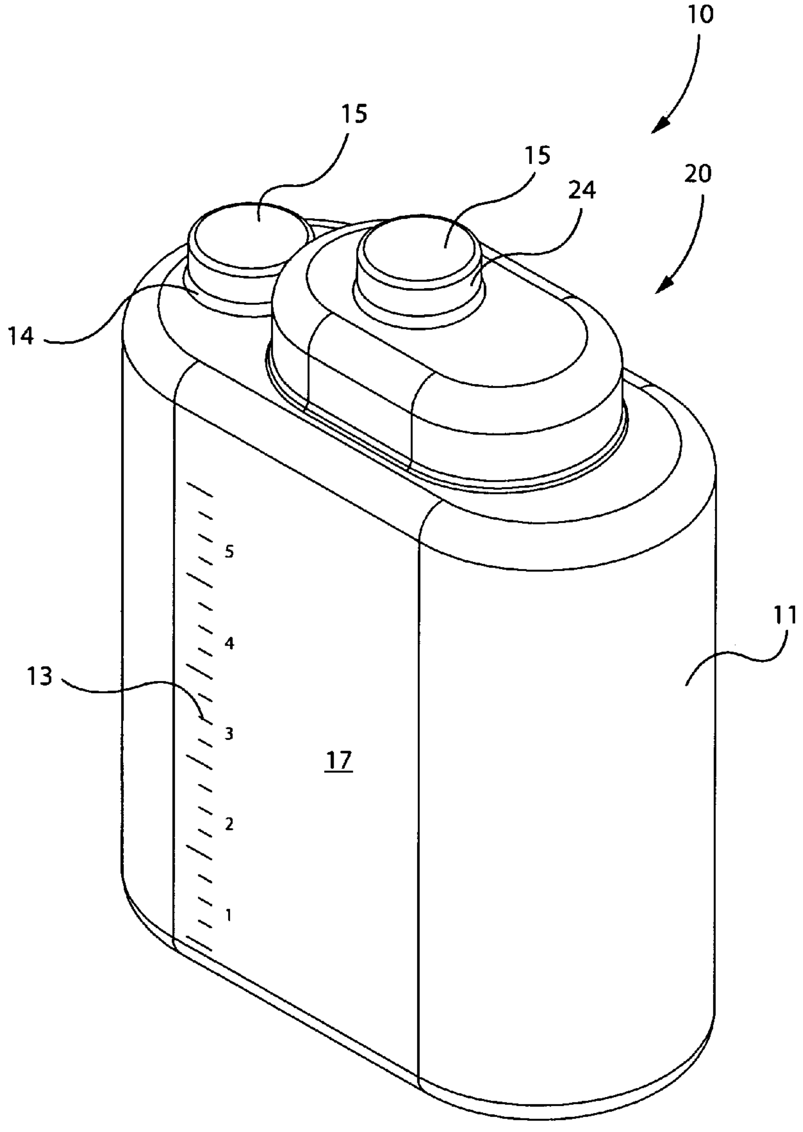
FIG. 1 is a perspective view showing a calibrated medicine mixing assembly, in accordance with the present invention.
Figure 2:
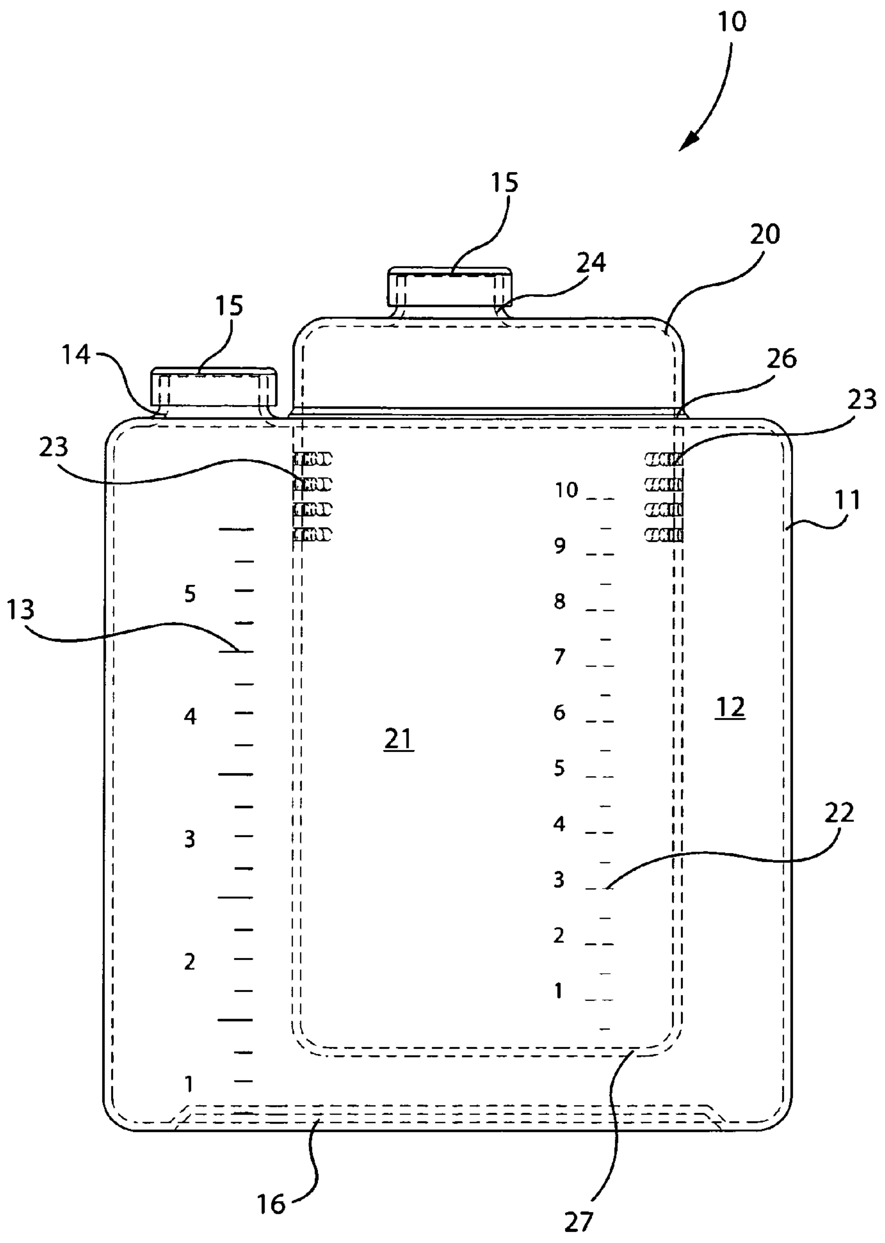
FIG. 2 is a front elevational view showing the primary and secondary reservoirs and the position of the orifices as shown in FIG. 1.
Figure 3:
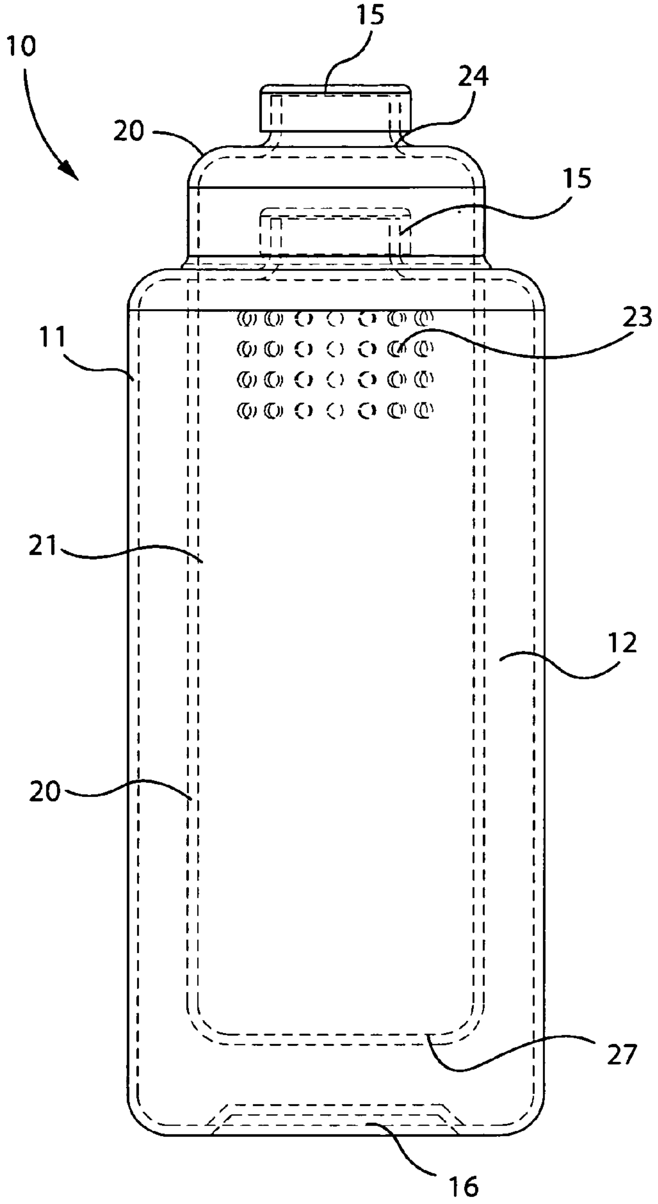
FIG. 3 is a side elevational view showing the orifices of the primary reservoir seated subjacent to a top surface of the secondary reservoir.
Figure 4:
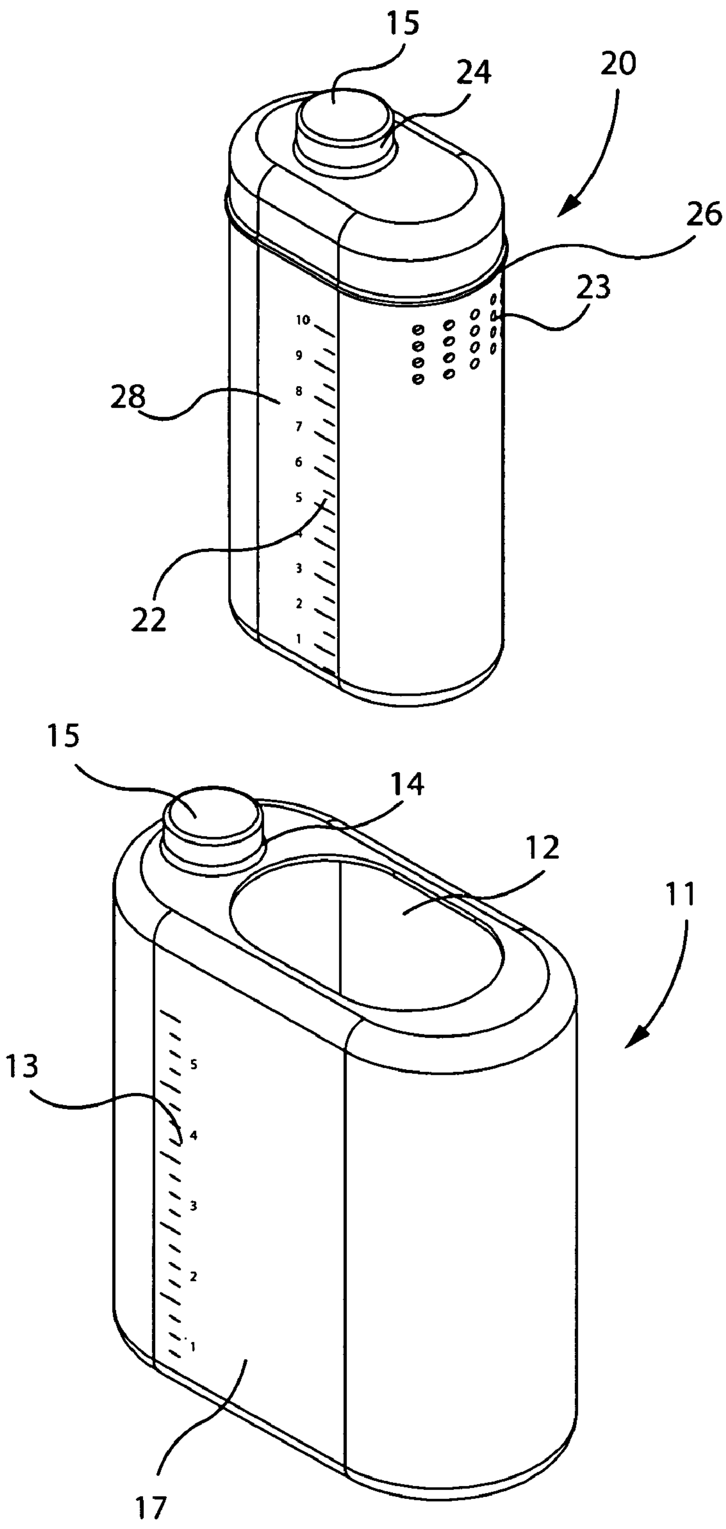
FIG. 4 is an exploded view showing the primary reservoir removed from the secondary reservoir.

The assembly of this invention is referred to generally in FIGS. 1-4 by the reference numeral 10 and is intended to provide a calibrated medicine mixing assembly 10 for assisting a user to accurately mix a powder agent with a fluid. It should be understood that while the calibrated medicine mixing assembly 10 may be used for assisting a user to accurately mix a medicinal powder agent with a fluid, many other different types of powder agents and fluids may be used, and this invention should not be limited to the uses described herein.

Referring to FIGS. 1-4 in general, the calibrated medicine mixing assembly 10 preferably includes a primary reservoir 11 having a primary cavity 12 adapted to receive the fluid. The primary reservoir 11 preferably includes calibrated fluid level indicia 13 displayed on an outer surface 17 thereof. Such an assembly 10 may further include a secondary reservoir 20 preferably having a secondary cavity 21 adapted to receive the powder agent. The secondary reservoir 20 preferably including calibrated level indicia 22 displayed on its outer surface 28.

The secondary reservoir 20 is further removably positioned into the primary reservoir 11 such that a major surface area of the secondary reservoir 20 is completely submerged inside the primary reservoir 11. A plurality of orifices 23 may preferably be formed along a top region of the secondary reservoir 20. Such orifices 23 may be situated inside the primary reservoir 11, thereby causing the secondary cavity 21 to be in fluid communication with the primary cavity 12 when the secondary reservoir 20 is situated within the primary reservoir 11.

In one embodiment, the secondary reservoir 20 may preferably be prohibited from laterally oscillating while seated within the primary reservoir 11 such as for example when the assembly 10 is held by a user. Each of the primary 11 and secondary 20 reservoirs may further include a primary reservoir top spout 14 and a secondary reservoir top spout 24 in fluid communication with a corresponding one of the primary cavity 12 and secondary cavity 21, respectively.

A cap 15 may further be removably coupled directly to a corresponding one of the top spouts 14, 24. Further, the primary cavity 12 may preferably extend downwardly from a top surface of the primary reservoir 11 and suitably sized and shaped to receive the secondary reservoir 20 therein. Further, the secondary reservoir 20 may include a unitary and continuous gasket 26 positioned along an entire perimeter. Such a gasket 26 flaring outwardly and away from the outer perimeter such that the gasket 26 directly sits on the top surface when the secondary reservoir 20 is situated within the primary reservoir 11. In this manner, the gasket 26 may preferably act as a seal to prevent the risk of spillage when the assembly 10 is inverted with the assembly held in place securely such as preferably with the index finger pressed against the top of the secondary spout 24 and the thumb and other fingers holding the primary reservoir 11 securely.

In another embodiment, the orifices 23 are further disposed subjacent to the top surface of the primary reservoir 11 to enable the powder agent and the fluid to mix when the primary reservoir 11 and secondary reservoir 20 are repeatedly inverted. The top spout 15 of the secondary reservoir 20 further remaining situated exterior of the primary reservoir 11 while the secondary reservoir 20 is situated within the primary cavity 12. In this way, the orifices 23 remain spaced below the top spout 15 and the top surface of the primary reservoir 11 while the secondary reservoir 20 is situated within the primary reservoir 11.

In a further embodiment, the secondary reservoir 20 is removed from the primary reservoir 11 when the secondary reservoir 20 is axially displaced along a linear path registered parallel to a longitudinal length of the primary reservoir. The assembly 10 further including a bottom-most surface of the secondary reservoir 20 to remain spaced above a bottom-most surface 16 of the primary cavity 12 while the secondary reservoir 20 is fully inserted into the primary reservoir 11 such that the fluid contained within the primary cavity 12 is able to freely travel beneath the secondary reservoir 20.

The invention further includes a method for accurately mixing a powder agent with a fluid, the method comprising the chronological steps of providing a primary reservoir 11 preferably having a primary cavity, including calibrated fluid level indicia 13 displayed on an outer surface 17.

The invention may further include the second step of providing a secondary reservoir 20 preferably having a secondary cavity 21 and preferably including calibrated powder agent level indicia 22 displayed on an outer surface 28 and provided with a plurality of orifices 23 formed along a top region of the secondary reservoir 20.

In this way, the assembly may enable pouring the fluid and powder agent into the primary cavity 12 and secondary cavity 21 respectively and removably positioning the secondary reservoir 20 into the primary reservoir 11 such that a major surface area of the secondary reservoir 20 is completely submerged inside the primary reservoir. This may preferably cause the secondary cavity 21 to be in fluid communication with the primary cavity 12 by situating the orifices 23 inside the primary reservoir 11 while the secondary reservoir 20 is situated within the primary reservoir. Such a method may preferably allow mixing the powder agent and the fluid by repeatedly inverting the primary and secondary reservoirs 11, 20; and prohibiting the secondary reservoir 20 from laterally oscillating while seated within the primary reservoir 11. Such a calibrated medicine mixing assembly 10 is vital and advantageous in allowing a user to provide the unexpected and unpredictable benefit of accurately measuring a medicinal powder and a fluid in exact quantities and enabling the combination to be properly mixed without spillage when the assembly 10 is repeatedly inverted so as to mix the ingredients thoroughly.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

Still referring to the figures in general, in an alternate embodiment, the reservoirs may include three separate units, including the same compartments as before, but not joined into one, and not meant to communicate their contents with one another. In this embodiment, one receives the prescription bottle of powdered medication, along with the two side compartments. The two side compartments may be removably attached to the center compartment by peel-n-stick adhesives. Users, again, follow precise directions for mixing the diluting agent, this time using either the cc or ml vial as a beaker, then pouring the diluting agent into the main compartment and shaking it vigorously to mix.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A calibrated medicine mixing assembly for assisting a user to accurately mix a powder agent with a fluid, said calibrated medicine mixing assembly comprising:

a primary reservoir having a primary cavity adapted to receive the fluid therein, said primary reservoir including calibrated fluid level indicia displayed on an outer surface thereof; and a secondary reservoir having a secondary cavity adapted to receive the powder agent therein, said secondary reservoir including calibrated powder agent level indicia displayed on an outer surface thereof;

wherein said secondary reservoir is removably positional into said primary reservoir such that a major surface area of said secondary reservoir is completely submerged inside said primary reservoir;

wherein said secondary reservoir is provided with a plurality of orifices formed along a top region thereof, said orifices being situated inside said primary reservoir and thereby cause said secondary cavity to be in fluid communication with said primary cavity while said secondary reservoir is situated within said primary reservoir;

wherein each of said primary and secondary reservoirs comprises:

a top spout in fluid communication with a corresponding one of said primary and secondary cavities respectively; and a cap removably coupled directly to a corresponding one of said top spouts respectively.

2. The calibrated medicine mixing assembly of claim 1, wherein said primary cavity extends downwardly from a top surface of said primary reservoir and is suitably sized and shaped to receive said secondary reservoir therein.

3. The calibrated medicine mixing assembly of claim 2, wherein said secondary reservoir comprises: a unitary and continuous gasket positioned along an entire perimeter thereof, said gasket flaring outwardly and away from said outer perimeter such that said gasket directly sits on said top surface when said secondary reservoir is situated within said primary reservoir.

4. The calibrated medicine mixing assembly of claim 2, wherein said orifices are disposed subjacent to said top surface of said primary reservoir to thereby enable the powder agent and the fluid to mix when said primary and secondary reservoirs are repeatedly inverted.

5. The calibrated medicine mixing assembly of claim 2, wherein said orifices remain spaced below said top spout and said top surface of said primary reservoir while said secondary reservoir is situated within said primary reservoir.

6. The calibrated medicine mixing assembly of claim 1, wherein said top spout of said secondary reservoir remains situated exterior of said primary reservoir while said secondary reservoir is situated within said primary cavity.

7. The calibrated medicine mixing assembly of claim 1, wherein said secondary reservoir is removed from said primary reservoir when said secondary reservoir is axially displaced along a linear path registered parallel to a longitudinal length of said primary reservoir.

8. The calibrated medicine mixing assembly of claim 1, wherein a bottom-most surface of said secondary reservoir remains spaced above a bottom-most surface of said primary cavity while said secondary reservoir is fully inserted into said primary reservoir such that the fluid contained within said primary cavity is able to freely travel beneath said secondary reservoir.

9. A calibrated medicine mixing assembly for assisting a user to accurately mix a powder agent with a fluid, said calibrated medicine mixing assembly comprising:

a primary reservoir having a primary cavity adapted to receive the fluid therein, said primary reservoir including calibrated fluid level indicia displayed on an outer surface thereof; and a secondary reservoir having a secondary cavity adapted to receive the powder agent therein, said secondary reservoir including calibrated powder agent level indicia displayed on an outer surface thereof;

wherein said secondary reservoir is removably positional into said primary reservoir such that a major surface area of said secondary reservoir is completely submerged inside said primary reservoir;

wherein said secondary reservoir is provided with a plurality of orifices formed along a top region thereof, said orifices being situated inside said primary reservoir and thereby cause said secondary cavity to be in fluid communication with said primary cavity while said secondary reservoir is situated within said primary reservoir;

wherein said secondary reservoir is prohibited from laterally oscillating while seated within said primary reservoir;

wherein each of said primary and secondary reservoirs comprises:

a top spout in fluid communication with a corresponding one of said primary and secondary cavities respectively; and a cap removably coupled directly to a corresponding one of said top spouts respectively.

10. The calibrated medicine mixing assembly of claim 9, wherein said primary cavity extends downwardly from a top surface of said primary reservoir and is suitably sized and shaped to receive said secondary reservoir therein.

11. The calibrated medicine mixing assembly of claim 10, wherein said secondary reservoir comprises: a unitary and continuous gasket positioned along an entire perimeter thereof, said gasket flaring outwardly and away from said outer perimeter such that said gasket directly sits on said top surface when said secondary reservoir is situated within said primary reservoir.

12. The calibrated medicine mixing assembly of claim 10, wherein said orifices are disposed subjacent to said top surface of said primary reservoir to thereby enable the powder agent and the fluid to mix when said primary and secondary reservoirs are repeatedly inverted.

13. The calibrated medicine mixing assembly of claim 10, wherein said orifices remain spaced below said top spout and said top surface of said primary reservoir while said secondary reservoir is situated within said primary reservoir.

14. The calibrated medicine mixing assembly of claim 9, wherein said top spout of said secondary reservoir remains situated exterior of said primary reservoir while said secondary reservoir is situated within said primary cavity.

15. The calibrated medicine mixing assembly of claim 9, wherein said secondary reservoir is removed from said primary reservoir when said secondary reservoir is axially displaced along a linear path registered parallel to a longitudinal length of said primary reservoir.

16. The calibrated medicine mixing assembly of claim 9, wherein a bottom-most surface of said secondary reservoir remains spaced above a bottom-most surface of said primary cavity while said secondary reservoir is fully inserted into said primary reservoir such that the fluid contained within said primary cavity is able to freely travel beneath said secondary reservoir.

* * * * *